US008865930B2

(12) United States Patent
Noel et al.

(10) Patent No.: US 8,865,930 B2
(45) Date of Patent: Oct. 21, 2014

(54) METHOD FOR MAKING TERPENE DERIVATIVES

(75) Inventors: Joseph P. Noel, San Diego, CA (US); Justin Ramsey, Vista, CA (US); Thomas J. Baiga, Escondido, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 511 days.

(21) Appl. No.: 12/737,739

(22) PCT Filed: Aug. 10, 2009

(86) PCT No.: PCT/US2009/053252
§ 371 (c)(1),
(2), (4) Date: Mar. 10, 2011

(87) PCT Pub. No.: WO2010/019489
PCT Pub. Date: Feb. 18, 2010

(65) Prior Publication Data
US 2011/0152563 A1 Jun. 23, 2011

Related U.S. Application Data

(60) Provisional application No. 61/088,654, filed on Aug. 13, 2008.

(51) Int. Cl.
C07C 69/74 (2006.01)
C07C 69/013 (2006.01)
C07C 67/00 (2006.01)
C07C 69/608 (2006.01)
C07C 69/78 (2006.01)
C07C 201/10 (2006.01)
C07C 205/03 (2006.01)
C07C 315/04 (2006.01)

(52) U.S. Cl.
CPC .............. *C07C 69/013* (2013.01); *C07C 67/00* (2013.01); *C07C 69/608* (2013.01); *C07C 69/78* (2013.01); *C07C 201/10* (2013.01); *C07C 205/03* (2013.01); *C07C 315/04* (2013.01); *C07C 2102/28* (2013.01)
USPC ........................................................ 560/127

(58) Field of Classification Search
None
See application file for complete search history.

(56) References Cited

U.S. PATENT DOCUMENTS

| 3,835,192 | A | 9/1974 | Van Der Linde et al. |
| 5,030,739 | A | 7/1991 | Foricher et al. |
| 6,200,786 | B1 | 3/2001 | Huang et al. |
| 7,129,271 | B2 | 10/2006 | Maupin et al. |
| 7,211,420 | B1 | 5/2007 | Wong et al |

OTHER PUBLICATIONS

Database Caplus Chemical Abstracts Service, Columbus, Ohio, US; Database Accession No. 1971:435259, Abstract of DE 2035901 May 13, 1971, Schulte-Elte et al.*
Database Caplus Chemical Abstracts Service, Columbus, Ohio, US; Database Accession No. 1990:36204, Abstract of Davies et al., Journal of the Chemical Society, Perkin Transactions 2: Physical Organic Chemistry (1972-1999) (1989), (7), 825-30.*
Database Caplus Chemical Abstracts Service, Columbus, Ohio, US; Database Accession No. 1978:615582, Abstract of Wilson et al., Journal of Agricultural and Food Chemistry (1978), 26(6), 1430-2.*
Andrus et al., "Copper catalyzed allylic oxidation of peresters," *Tetrahedron* 58:845-866, 2002.
Chen et al., "Serial Ligand Catalysis: A Highly Selective Allylic C-H Oxidation," *Journal of the American Chemical Society* 127(19):6970-6971, 2005.
Davies et al., "The Rearrangement of Allylic Hydroperoxides Derived from (+)-Valencene," *Journal of the Chemical Society, Perkins Transcript 2*, pp. 825-830, 1989.
Nemoto et al., "Pd-Catalyzed Asymmetric Allylic Amination of Morita-Baylis-Hillman Adduct Derivatives Using Chiral Diaminophosphine Oxides: DIAPHOXs," *Organic Letters* 9(5):927-930, 2007.

(Continued)

*Primary Examiner* — Karl J Puttlitz
(74) *Attorney, Agent, or Firm* — Klarquist Sparkman, LLP

(57) ABSTRACT

Disclosed herein is a method for synthesizing terpenoid compounds, as well as compositions comprising terpenoids and methods for their use. In one aspect the process is represented by the scheme

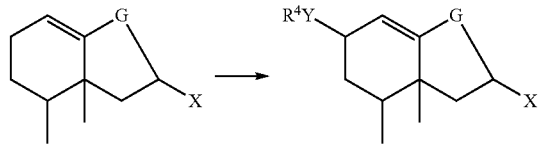

wherein G is

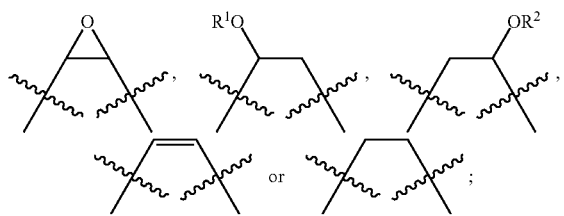

X is

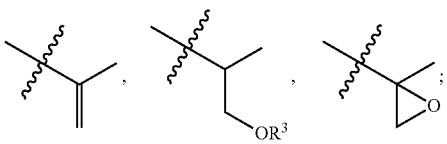

and
$R^1$, $R^2$ and $R^3$ independently are selected from H, acyl, lower alkyl and aralkyl; and
Y is —O—, —S— or —NH—, and $R^4$ is selected from H, acyl, lower alkyl and aralkyl.

15 Claims, No Drawings

(56) References Cited

OTHER PUBLICATIONS

Sigma-Aldrich, "The Growing Impact of Asymmetric Catalysis," *Aldrichimica Acta* 40(3):56-91, 2007.
Shaw et al., "Synthesis, Crystal Structures, and Laser Flash Photolysis of *tert*-Butyl Aroylperbenzoates," *Journal of Organic Chemistry* 68(22):8368-8372, 2003.
Trost, "Asymmetric Allylic Alkylation, an Enabling Methodology," *Journal of Organic Chemistry* 69(18):5813-5837, 2004.
Wilson et al., "Synthesis of Nootkatone from Valencene," *Journal of Agricultural and Food Chemistry* 26(6):1430-1432, 1978.
International Search Report dated Mar. 22, 2010, from International Application No. PCT/US2009/053252.

* cited by examiner

METHOD FOR MAKING TERPENE DERIVATIVES

CROSS REFERENCE TO RELATED APPLICATIONS

This is the U.S. National Stage of International Application No. PCT/US2009/053252, filed Aug. 10, 2009, which was published in English under PCT Article 21(2), which in turn claims the benefit of U.S. Provisional Application No. 61/088,654, filed Aug. 13, 2008. The provisional application is incorporated herein in its entirety.

ACKNOWLEDGMENT OF GOVERNMENT SUPPORT

This invention was made with the support of grant number GM054029-08, awarded by the National Institutes of Health. The government has certain rights in the invention.

FIELD

Disclosed herein is a method for synthesizing terpenoid compounds, as well as compositions comprising terpenoids and methods for their use.

BACKGROUND

Terpenoid compounds are a class of compounds formally assembled from terpene building blocks. Naturally occurring terpenoids constitute one of the largest classes of natural products compounds. Such terpenoids have significant commercial value in the perfume and flavoring industries and as starting materials for the chemical industry. Many members of the terpenoid class are biologically active, with notable compounds having antibacterial or antifungal activity; this potential for biological activity has attracted the interest of the pharmaceutical industry.

Terpenoids of commercial interest often are not naturally occurring, but rather derivatives which commonly require regioselective or stereoselective functionalization at allylic or non-activated carbon-hydrogen bonds of the parent terpene. This type of chemical transformation can be difficult to carry out by conventional methods because the highly reactive chemical oxidizing agents typically used lack selectivity and may preferentially attack other carbon-hydrogen bonds and reactive functional groups, such as olefinic double bonds commonly present in terpenes.

SUMMARY

Disclosed herein is a method for making modified terpenoid compounds from a terpene substrate having an alkene moiety as well as at least one other group susceptible to oxidation, for example a second alkene moiety. The terpene derivative is produced for example by selectively oxidizing an allylic carbon of the terpene substrate.

In one aspect this process is represented by general Scheme 1:

Scheme 1

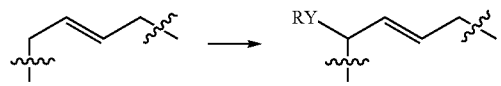

wherein Y is —O—, —S— or —NH—, and R is selected from H, acyl, lower alkyl and aralkyl. The transformation illustrated above formally results in an allylic oxidation, but also may include other steps in addition to allylic oxidation, including, without limitation, substitution, alkylation, acylation and the like.

In another aspect of the disclosed method, producing an oxidized terpene derivative entails oxidizing a terpenoid of the formula

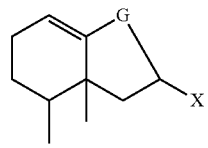

wherein G is

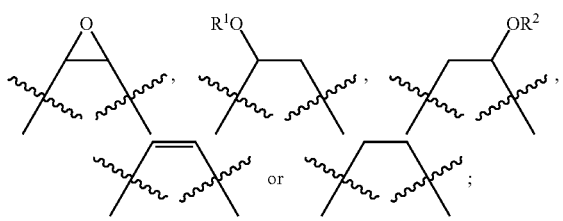

X is

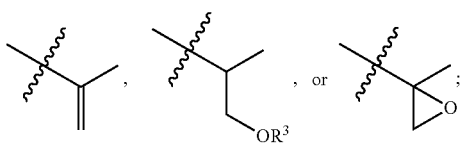

and $R^1$, $R^2$ and $R^3$ independently are selected from H, acyl, lower alkyl and aralkyl; and producing an oxidized terpene derivative having the formula

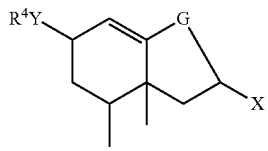

wherein Y is —O—, —S— or —NH—, and $R^4$ is selected from H, acyl, lower alkyl and aralkyl.

Also disclosed herein are compounds and compositions produced according to the described method. The compounds and compositions produced according to the method, as well as the methods and other objects, features, and advantages of the invention, will become more apparent from the following detailed description.

DETAILED DESCRIPTION

I. Terms and Abbreviations

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Optional" or "optionally" means that the subsequently described event or circumstance can but need not occur, and that the description includes instances where said event or circumstance occurs and instances where it does not. The term "comprises" means "includes." The abbreviation, "e.g." is derived from the Latin exempli gratia, and is used herein to indicate a non-limiting example. Thus, the abbreviation "e.g." is synonymous with the term "for example." Although methods and materials similar or equivalent to those described herein can be used in the practice or testing of this disclosure, suitable methods and materials are described below. In addition, the materials, methods, and examples are illustrative only and not intended to be limiting.

As used herein the term "alkyl" refers to an aliphatic group that is branched or unbranched and is a saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). Exemplary haloalkyl groups include perhaloalkyl groups, wherein all of the hydrogen atoms present on the group have been replaced with a halogen, for example perfluoromethyl refers to the group —$CF_3$. The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom in the ring such as, but not limited to, nitrogen, oxygen, sulfur, or phosphorous. In contrast with heterocycloalkyl groups, the term "alicyclic" refers to a group that is both aliphatic and cyclic. Such groups contain one or more saturated or unsaturated all-carbon rings, which are not aromatic. Alkyl groups, including cycloalkyl groups and alicyclic groups optionally may be substituted. The nature of the substituents can vary broadly. Typical substituent groups useful for substituting alkyl groups in the presently disclosed compounds include halo, fluoro, chloro, alkyl, alkylthio, alkoxy, alkoxycarbonyl, arylalkyloxycarbonyl, aryloxycarbonyl, cycloheteroalkyl, carbamoyl, haloalkyl, dialkylamino, sulfamoyl groups and substituted versions thereof.

The term "alkenyl" refers to a hydrocarbon group of 2 to 24 carbon atoms and structural formula containing at least one carbon-carbon double bond.

The term "alkynyl" refers to a hydrocarbon group of 2 to 24 carbon atoms and a structural formula containing at least one carbon-carbon triple bond.

The term "aliphatic" refers to moieties including alkyl, alkenyl, alkynyl, halogenated alkyl and cycloalkyl groups as described above. A "lower aliphatic" group is a branched or unbranched aliphatic group having from 1 to 10 carbon atoms.

The term "amine" or "amino" refers to a group of the formula —NRR', where R and R' may be the same or different and independently are hydrogen or an alkyl, alkenyl, alkynyl, aryl, aralkyl, cycloalkyl, halogenated alkyl, or heterocycloalkyl group described above.

The term "amide" refers to a group represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. The term "alkyl amino" refers to alkyl groups as defined above where at least one hydrogen atom is replaced with an amino group.

The term "aralkyl" refers to an aryl group having an alkyl group, as defined above, attached to the aryl group. An example of an aralkyl group is a benzyl group.

Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

The term "carboxyl" refers to a —COOH radical. Substituted carboxyl refers to —COOR where R is aliphatic, heteroaliphatic, alkyl, heteroalkyl, aralkyl, aryl or the like.

The term "derivative" refers to compound or portion of a compound that is derived from or is theoretically derivable from a parent compound.

The term "hydroxyl" refers to a moiety represented by the formula —OH. The term "alkoxy group" is represented by the formula —OR, wherein R can be an alkyl group, optionally substituted with an alkenyl, alkynyl, aryl, aralkyl, cycloalkyl, halogenated alkyl, or heterocycloalkyl group as described above.

The term hydroxyalkyl refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can be substituted with aryl, optionally substituted heteroaryl, aralkyl, halogen, hydroxy, alkoxy, carboxyalkyl, optionally substituted cycloalkyl, optionally substituted cycloalkenyl and/or optionally substituted heterocyclyl moieties.

The term "isoprenoid" as used in the technical literature refers to compounds which in a more or less apparent manner might be obtainable by combining isoprene units. The term isoprenoid therefore embraces subgroups such as hemiterpenes, terpenes, sesquiterpenes, diterpenes, sesterterpenes, triterpenes, tetraterpenes, carotenoids, steroids and the like. The terpenes, sesquiterpenes, diterpenes, sesterterpenes, triterpenes and tetraterpenes as well as similar compounds with an isoprenoid structural basis are also classified under the term terpenoids. With respect to the terms carotenoid, isoprenoid, steroid, terpenoid and the like, reference is made to Römpps Chemie Lexikon, especially volume 1, 609 (1979), volume 3, 1965 (1983), volume 5, 3336 (1975) and volume 6, 3504 (1977), which is incorporated herein by reference.

Isoprenoids are derived, formally or from the assembly of isoprene units. Substances with 10, 15, 20, 30 and 40 carbon atoms in the empirical formula are more predominant than others in nature and moreover have methyl substituents in very specific positions of their structure, prompting Ruzicka to formulate the "isoprene rule". Accordingly, isoprenoids include the compounds described in greater detail under specific entries, namely hemiterpenes, terpenes, iridoids, sesqui-, di-, sester- and triterpenes, carotenoids, steroids and in particular naturally occurring substances, a prime example being dolichol. However, synthetic polyisoprene, for example, is generally not considered an isoprenoid, but natural rubber, balata and gutta percha are. Many non-isoprenoid natural substances have isoprenoids in their side chains with examples including tocopherols, vitamin K, and ubiquinone (multiprenyl chains) and chlorophyll.

The above terms isoprenoid, steroid, terpenoid, terpene, sesquiterpene etc embrace not only hydrocarbons with an isoprenoid structural basis, but also ethers, aldehydes, ketones and esters derived therefrom. Preferred intermediates in the disclosed process, for example, isolable intermediates produced by the oxidation of a terpene substrate are the isoprenoid hydrocarbons and the alcohols or esterified alcohols derived therefrom, for example compounds with a group RO— in which R denotes hydrogen or an acyl group.

The term "lower alkyl" refers to an alkyl group containing from one to ten carbon atoms substituted with one or more hydroxy (—OH) moieties.

The term "sulfide" refers to a moiety represented by the formula —SR, wherein R can be an alkyl group, optionally substituted with an alkenyl, alkynyl, aryl, aralkyl, cycloalkyl, halogenated alkyl, or heterocycloalkyl group as described above.

The term "sulfonyl" refers to the radical —SO$_2$—. The sulfonyl group can be further substituted with a variety of groups to form, for example, sulfonic acids, sulfonamides, sulfonate esters and sulfones.

II. Method for Making Terpene Derivatives

Disclosed herein is a method for making modified terpenoid compounds from a terpene substrate having an alkene moiety as well as at least one other group susceptible to oxidation, for example a second alkene moiety; and producing the oxidized terpene derivative by selectively oxidizing an allylic carbon of the terpene substrate.

In one aspect this process is represented by general Scheme 1:

Scheme 1

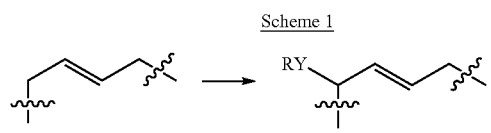

which illustrates a fragment of a larger terpene substrate being functionalized at the allylic position. With continued reference to the scheme, Y is —O—, —S— or —NH—, and R is selected from H, acyl, lower alkyl and aralkyl. The transformation illustrated above formally results an allylic oxidation, but also may include other steps in addition to allylic oxidation, including, without limitation, substitution, alkylation, acylation and the like. The following discussion will illustrate the terpenes substrates suitable for use in the method as well as the conditions suitable for the terpene modifications desired, in particular allylic oxidation and alkylation.

A. Terpene Starting Materials

Although the terpenes used in the present method generally have the formula $(C_5H_8)_n$ where n is 2 or more, especially 2, 3 or 4, it is to be understood that the term "terpene" extends to compounds which are referred to as "terpenoid", involving the loss or shift of a fragment, generally a methyl group. Thus, for example, sesquiterpenes (where n is 3) that can be used in the present invention may contain only, for example, 14, rather than 15, carbon atoms, and such compounds are considered to be terpenoid or, more specifically, sesquiterpenoid. Generally the terpene is one which can be assembled synthetically and/or biosynthetically from isoprene units. The terpene may be cyclic or acyclic.

The rings which may be present in the terpenes will typically have from 3 to 9 carbon atoms, more especially 5 or 6 carbon atoms. Thus, in particular, the terpenes will contain a cyclohexane, cyclohexene or cyclohexadiene ring.

The terpenes will generally contain a total of 3 or 4 exocyclic methyl or methylene groups, for example 2 methyl groups and 1 methylene group or 3 methyl groups for a monoterpene, and 3 methyl groups and 1 methylene group or 4 methyl groups for a sesquiterpene.

When the terpene or terpenoid includes a cycloalkene, the cycloalkene generally comprises up to 9 ring members, typically a 5, 6, 7, 8, 9-membered ring. In exemplary embodiments, the cycloalkene is a cyclohexene.

Monoterpenes (having the formula above, where n is 2) will generally have 10 carbon atoms, typically with 1 to 3 double bonds, especially 1 or 2 ring double bonds, and typically with 0, 1 or 2 rings. It is possible for one of the rings to be formed as a bridge containing, typically 0 or 1 carbon atoms. In other words, it can be formed by a direct link between 2 carbon atoms of an existing ring, for example as in fused ring compounds, or with an intermediate methylene group. If the terpene is acyclic it will generally contain at least 2 double bonds and more typically 3 double bonds.

Particular examples of monoterpenes employed in the present method typically include, without limitation, a limonene, pinene, terpinene, sabinene, thujene, mercene, ocimeme, nerol or geraniol. Although limonene refers to a specific structure illustrated below, such common names for this and other terpenes, refers to all stereoisomers of the compound unless is otherwise apparent from context.

Diterpenes also are employed in the presently disclosed method. Suitable diterpenes (where n is 4) include, without limitation, casbene, retinal, abietic acid or a gibberellin.

Sesquiterpenes are particularly useful compounds in the present method. Generally sesquiterpenes formed by a head-to-tail arrangement of three isoprene units. Sesquiterpenes employed herein will normally contain 14 or 15 carbon atoms, typically with 1 or 2 double bonds and typically 1 to 3 rings, with the possibility of fused rings and/or bridged rings. The sesquiterpene is typically an aromadendrene, caryophyllene, longifolene, valencene, isobazzanene, silphinene, ishwarane, isopatchchoul-3-ene, or isosesquicarene.

Particular examples of terpene substrates include, without limitation, the following:

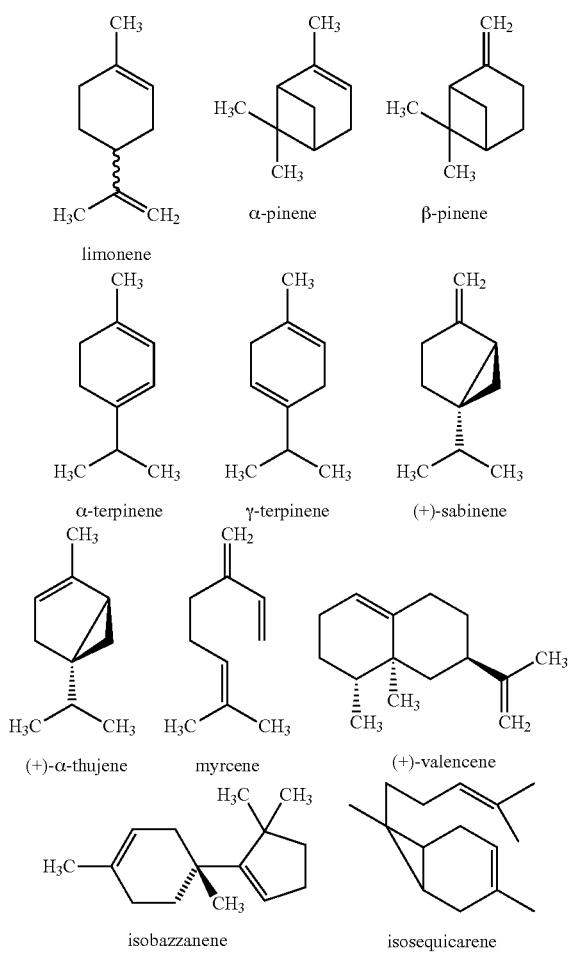

Substituted derivatives of any of the terpenes or cycloalkenes mentioned above may also be used. Typically 1, 2, 3 or more substituents are present. Any combination of the following substituents, for example one or more halogen atoms, aliphatic groups, such as an alkyl or alkenyl group, which generally has 1 to 6 carbons. Examples of alkyl and alkenyl groups include those substituted with one or more halogens.

Exemplary halogenated terpene substituents have the formula $C_nH_kX_m$, wherein X is the halogen, n is 1, 2, 3 or more, m is 1, 2, 3, 4 or more and k is an integer of an appropriate value so that the valences of the substituent $C_nH_kX_m$ are satisfied. By way of example, an alkyl substituent may have the values so that $k+m=2n+1$. Typically k is 1, 2, 3, 4 or more, or may be 0, for example where the substituent is a perhaloalkyl group. The halogen is typically fluorine, chlorine or bromine Contemplated terpene substituents may also comprise 1, 2 or more oxygen atoms and for example may be an alcohol, aldehyde, ketone or epoxide group.

B. Allylic Oxidation and Alkylation

In one embodiment the disclosed method for making terpene derivatives follows Scheme 2:

Scheme 2

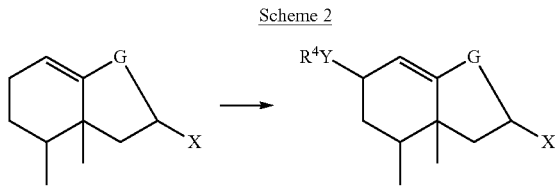

wherein G is

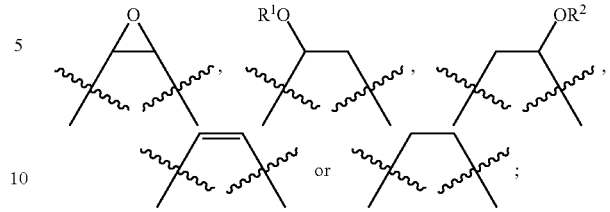

X is

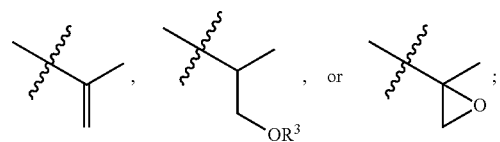

and $R^1$, $R^2$ and $R^3$ independently are selected from H, acyl, lower alkyl and aralkyl; and Y is —O—, —S— or —NH—, and $R^4$ is selected from H, acyl, lower alkyl and aralkyl.

In certain embodiments the Scheme illustrated above can be thought of as a first step in a process for making terpene derivatives encompassing at least two steps. Depicted in Scheme 2 is a first, allylic oxidation step. A second optional step embodied by the disclosed method includes alkylation of the product formed in Scheme 2, such that an allylic alkylation is performed. In one aspect the oxidation step, such as is set forth in Scheme 2, produces an oxidized terpene derivative of the formula

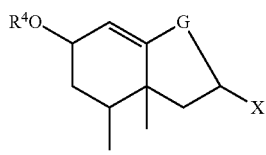

wherein G is

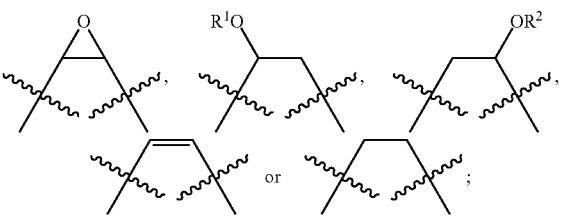

X is

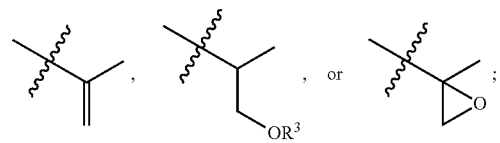

and $R^1$, $R^2$, $R^3$ and $R^4$ independently are selected from H, acyl, lower alkyl and aralkyl. Thus, in the Scheme 2, the allylic carbon of the terpene substrate is oxidized by an allylic C—H with an allylic carbon heteroatom bond, such as a C—O. In one such embodiment the product of Scheme 2 can be represented by the formula

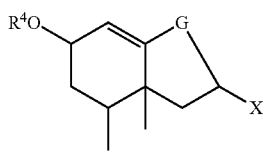

In one embodiment the oxidation causes the formation of a C—O bond in the compound, generally as the hydroxide from the oxidation of a carbon-hydrogen bond, but an epoxide may be formed from the oxidation of a carbon-carbon double bond. The oxidation may thus introduce a hydroxy, aldehyde, ketone or epoxide group. Alternatively the oxidation may cause the further oxidation of an oxygen-containing group, such as converting a hydroxy group into an aldehyde or ketone group. One, two or more carbon atoms may be oxidized in the same substrate molecule.

The oxidation may give rise to 1, 2 or more oxidation products. These different products may result from the introduction of a new stereocenter, from different carbon atoms being attacked and/or from different degrees of oxidation occurring at a given carbon atom.

The oxidation may occur on either a ring carbon atom or a substituent carbon atom or both. At least the initial oxidation will involve attack of a C—H bond which may be activated or non-activated or attack at a carbon-carbon double bond (typically giving an epoxide). Generally an activated C—H bond is where the carbon atom is in a benzylic or allyl position. Aromatic rings and olefinic double bonds activate C—H bonds to attack by stabilizing the radical intermediate or any build-up of charge generated during the reaction pathway. The carbon of the C—H bond may be a primary, secondary or tertiary carbon.

The oxidation typically preserves stereoisomerism, but also typically introduces a new stereocenter. In one aspect of the method the new stereocenter is introduced selectively, thus when the substrate consists of a single stereoisomer the product typically consists of a single corresponding stereoisomer, or can contain a preponderance of the corresponding stereoisomer. But in other embodiments a new stereocenter is formed nonselectively. Thus, introduction of a new stereocenter can result in the production of diastereomers.

In one aspect of the disclosed method, isoprenoids having an allylic hydrogen atom, such as isoprenoids that possess a methyl, methylene or methyne group on a C—C double bond are oxidized. Suitable starting materials include, without limitation, naturally occurring terpenes, but also can include synthetic or partially synthetic terpenoid compounds. Preferred starting materials in the process in accordance with the invention are the steroids, terpenes and sesquiterpenes which have at least one allylic hydrogen atom.

Methods disclosed herein for selectively oxidizing the terpene compounds include the Kharasch-Sosnovsky reaction. The Kharasch-Sosnovsky reaction employs a copper catalyst and a stoichiometric perester oxidant to accomplish allylic oxidation. The Kharasch-Sosnovsky reaction as employed herein provided the desired regioselectivity and chemoselectivity for preparing terpene derivatives.

Another method for oxidizing the terpene compounds to produce terpenoid derivatives according to the present disclosure is the White reaction. The White reaction is a Pd-mediated catalytic process that is both regioselective and mild. The conditions disclosed by White and coworkers in *J. Am. Chem. Soc.* 2005, 127, 6970-6971, which is incorporated herein by reference, were found to work well in the present method for producing terpene derivatives.

With reference again to Scheme 2, after allylic oxidation, a second step can involve allylic alkylation of an oxidized intermediate. One example, is an allylic alkylation of the product of Scheme 2 as set forth in Scheme 3:

Scheme 3

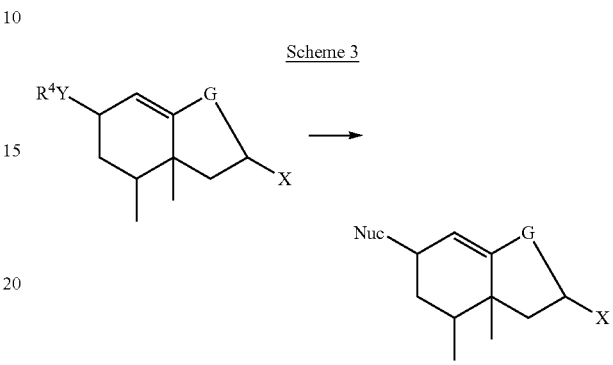

wherein Nuc represents a nucleophilic moiety. The transformation illustrated in Scheme 3 typically is a transition metal mediated reaction, such as a palladium-mediated reaction. In one embodiment the transformation is accomplished in one embodiment via a Tsuji-Trost reaction, namely the palladium-catalyzed allylation of a nucleophilic moiety. Both hard and soft nucleophiles can be added by the Tsuji-Trost reaction, although typically the method disclosed herein employs nucleophiles that would be considered soft nucleophiles. Soft nucleophiles are known to those of ordinary skill in the art of synthetic chemistry and generally include those derived from conjugate acids with a pKa<25. Such nucleophiles normally add directly to the allyl moiety, whereas hard nucleophiles first attack the metal center, followed by reductive elimination to give the allylation product.

In one embodiment a suitable carbon nucleophile is represented by the formula

wherein A and B independently are the same or different electron withdrawing groups. In other embodiments the nucleophile is a nitrogen nucleophile, such as $HNR^5R^6$, or $R^7N_3$; wherein $R^5$ and $R^6$ independently are selected from H, lower alkyl, aralkyl, acyl and sulfonyl; and $R^7$ is H or silyl.

Further illustration of the conditions and reagents for the alkylation reaction of Scheme 3 is found in the following references: V. Jagadeshwar, B. Saritha, C. Narsihmulu, S. Chandrasekhar Palladium-Triethylborane-Triggered Direct and Regioselective Conversion of Allylic Alcohols to Allyl Phenyl Sulfones *J. Org. Chem.*, 2005, 70, 6506-6507; O. G. Mancheno, J. Priego, S. Cabrera, R. G. Arrayas, T. Llamas, J. C. Carretero, 1-Phosphino-2-sulfenylferrocenes as Planar Chiral Ligands in Enantioselective Palladium-Catalyzed Allylic Substitutions. *J. Org. Chem.*, 2003, 68, 3679-3686; T. Nemoto, T. Matsumoto, T. Masuda, T. Hitomi, K. Hatano, Y. Hamada, P-Chirogenic Diaminophosphine Oxide: A New Class of Chiral Phosphorus Ligands for Asymmetric Catalysis. *J. Am. Chem. Soc.*, 2004, 126, 3690-3691; B. M. Trost, D.

L. Van Vranken, Asymmetric Transition Metal-Catalyzed Allylic Alkylations. *Chem. Rev.* 1996; 96 395-422; B. M. Trost Asymmetric Allylic Alkylation, an Enabling Methodology. *J. Org. Chem.* 2004, 69, 5813-5837; and B. M. Trost and D. R. Fandrick Palladium-Catalyzed Dynamic Kinetic Asymmetric Allylic Alkylation with the DPPBA Ligands. *Aldrichimica Acta* 2007, 40, 59-72; each of these publications is incorporated herein by reference.

Typically the alkylation reactions employed in certain embodiments, including examples of reactions described in Scheme 3, are catalyzed by palladium. Similar reactions using other metals, including molybdenum and iridium-based catalysts are known to those of skill in the art. Palladium catalysts are particularly useful for alkylation of nucleophiles of the formula

In one embodiment of the disclosed method for making terpene derivatives, alkylation of this nucleophile yields a compound of the formula

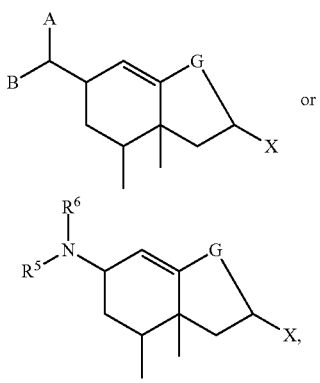

In the reactions illustrated by Scheme 3, the compound

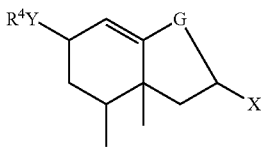

produced via selective allylic oxidation as described herein has the formula

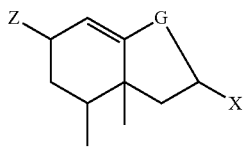

wherein Z is or is converted into a leaving group. For example, Z may be, without limitation, a halide, such as chloride, bromide or iodide, an ester group, e.g. of the formula $R^5COO$—, or a sulfonyl group, such as a mesyl, nosyl or tosyl group.

Thus, in certain embodiments an oxidized terpene derivative used for further modification, for example as in Scheme 3, has the formula

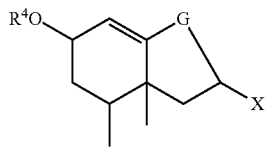

Wherein $R^4O$— is or is converted into a leaving group such that the illustrated compound is an alkylating agent. For example, $R^4$ may be a sulfonyl group an acyl group or the like. In particular examples wherein $R^4$ is acyl the oxidized terpene derivative has the formula

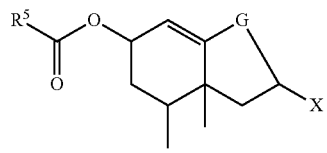

wherein typically $R^5$ is optionally substituted lower alkyl or optionally substituted aryl.

In one embodiment, reaction illustrated in Scheme 2, produces a compound of the formula

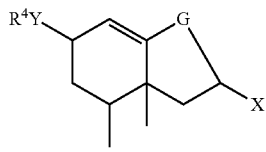

wherein $R^4Y$— is an acyl group or a sulfonyl group. In other embodiments the $R^4Y$— group is converted to a leaving group such as an acyl group or a sulfonyl group. In still other examples an oxidized terpene derivative wherein $R^4$ is acyl or sulfonyl is transesterified to produce a new transesterified ester or sulfonate ester. As is known to those of skill in the art of synthetic chemistry the $R^4$ group can be readily varied, for example by transesterification chemistry, to produce a compound having different properties for further modification or for use, for example as a perfume or flavoring.

In particular examples the terpene derivatives disclosed herein have the formula

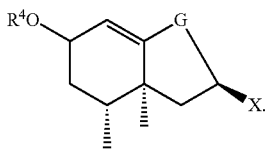

In still other examples the compounds disclosed herein have the formula

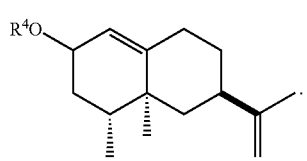

More particularly, examples of terpene derivatives disclosed herein include, without limitation those having the formula

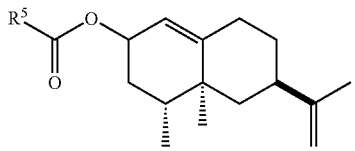

wherein $R^5$ represents an optionally substituted alkyl group or an optionally substituted aryl group.

Exemplary compounds prepared according to the methods disclosed herein include those of the formula

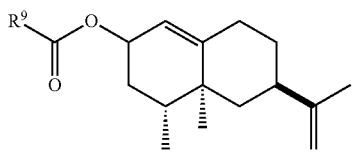

wherein $R^9$ represents an optionally substituted lower alkyl group.

Still other examples have the formula

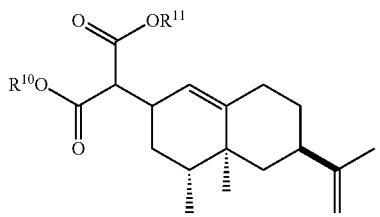

wherein $R^{10}$ and $R^{11}$ independently are selected from lower alkyl groups.

III. Examples

The foregoing disclosure is further explained by the following non-limiting examples.

Example 1

This example describes the benzoylation of valencene on 0.1 mmol scale via Kharasch-Sosnovsky reaction according to the Scheme 4:

Scheme 4

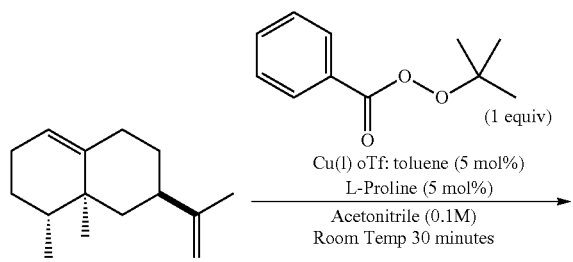

(1 equiv)

Cu(I) oTf: toluene (5 mol%)
L-Proline (5 mol%)
Acetonitrile (0.1M)
Room Temp 30 minutes -continued

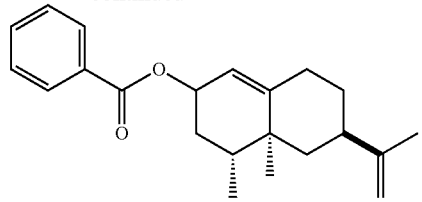

To a flame dried and nitrogen purged 100 mL round bottom flask equipped with a magnetic stir bar is added freshly distilled acetonitrile, valencene, Cu(I))Tf catalyst, L-proline, and t-butyl peroxybenzoate. The reaction was stirred at room temperature under nitrogen for approximately 30 minutes. Reaction progress was checked by thin layer chromatography (TLC) in 4:1 hexanes:ethyl acetate with UV visualization at 254 nM (valencene Rf≈0.83; product Rf≈0.46). Once the starting material was completely consumed as judged by TLC, the acetonitrile was concentration to dryness via rotary evaporation. The residue was dissolved in ≈30 mL ethyl acetate, and the ethyl acetate was then transferred to a separatory funnel. The ethyl acetate was washed twice with 50 mL of saturated sodium chloride and was then dried of sodium sulfate. The dried ethyl acetate was then concentrated via rotary evaporation to yield ≈300 milligrams of product as a clear pale yellow oil. The final product can be further purified by column chromatography on silica, eluting with 10:1 hexanes:ethyl acetate. The general method for this protocol is Lashley and Andrus, *Tetrahedron* 2002, 58, 845-866, which is incorporated herein by reference.

Example 2

This example describes the preparation of 3-methoxyphenylacetyl perbenzoate on 0.1 mmol scale according to the method of Shah and Neckers *J. Org. Chem.* 2003, 68, 8368-8372, which is incorporated herein by reference, and illustrated below by Scheme 5:

Scheme 5

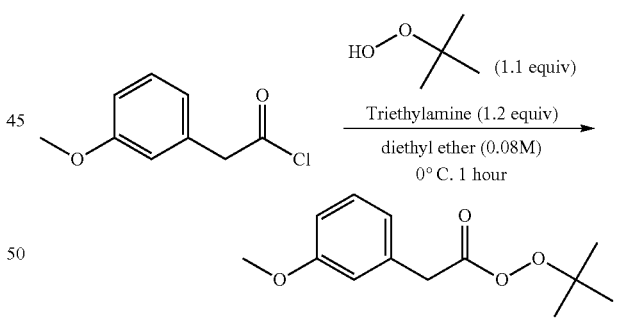

To a flame dried nitrogen purged 5 mL round bottom flask equipped with a magnetic stir bar was added 1 mL of dry diethyl ether and 3-methoxyphenylacetyl chloride. The mixture was cooled in an ice water bath with constant stirring under nitrogen. To a separate flame dried, nitrogen purged 5 mL round bottom flask equipped with a magnetic stir bar was added 250 μL of dry diethyl ether, t-butylhydroperoxide and triethylamine. This mixture also was cooled in an ice water bath with constant stirring under nitrogen. Once both mixtures were at 0° C., the t-butylhydroperoxide mixture was added to the 3-methoxyphenylacetyl chloride mixture. The subsequent reaction was monitored by TLC using 2:1 hexanes:ethyl acetate and 254 nm UV visualization (3-methoxyphenylacetyl chloride Rf≈0.18; product Rf≈0.55). Once the reaction was complete it was filtered through a short plug of silica gel and eluted with 20 mL dry dethyl ether. The filtrate ether was then concentrated to yield the product peroxide as a clear pale yellow oil. The product can be further purified via silica gel chromatography eluting with 4:1 hexanes:ethyl acetate.

Example 3

This example describes the derivatization of the benzoylated valencene intermediate prepared in Example 1 on 0.39 mmol scale. The mechanism of alkylation reactions of this type are described by Trost *J. Org. Chem.* 2004, 69, 5813-5837, which is incorporated herein by reference and as illustrated by Scheme 6:

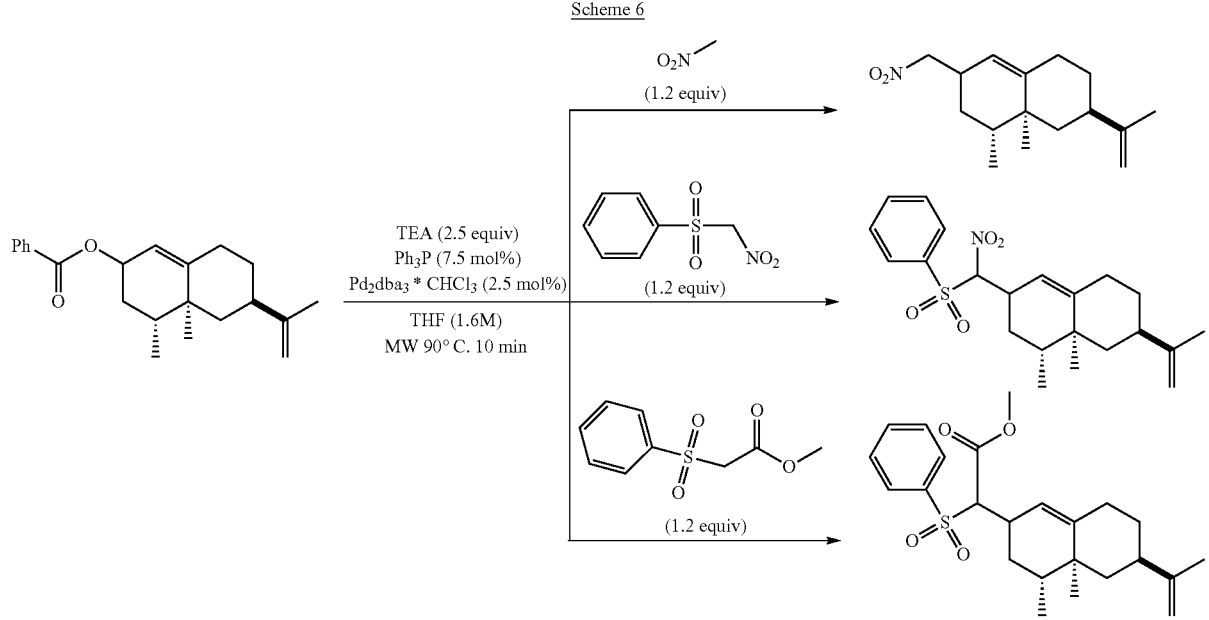

With reference to the Scheme 6 above, to three flame dried 5 mL microwave vials was added benzoylated valencene, triethylamine, triphenylphosphine, Pd$_2$ dba.CHCl$_3$ and THF. To the first vial was added nitromethane, to the second, phenylsulfonylnitromethane, and to the third methylphenyl sulfonylacetate. Each vial was capped and sealed under nitrogen and placed under microwave irradiation at 90° C. for 10 minutes. The product purity was assessed by LC/MS.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A terpene derivative according to the formula

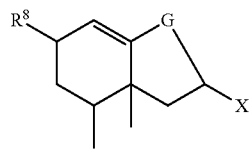

wherein G is

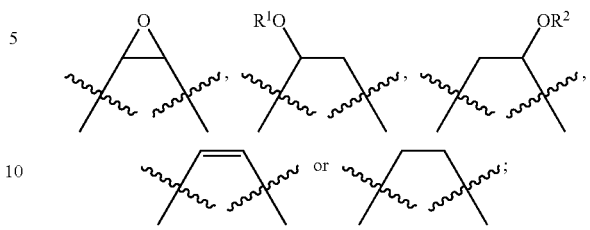

X is

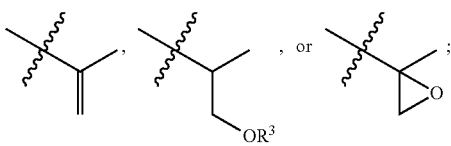

and

R$^1$, R$^2$ and R$^3$ independently are selected from H, acyl, lower alkyl or aralkyl;

R$^8$ represents

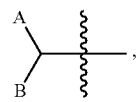

—NR$^5$R$^6$, OR$^4$ or —N$_3$, wherein A and B independently are selected from an ester, an aromatic sulfonyl, a nitro or hydrogen;

R$^4$ is independently selected from lower alkyl or aralkyl; and

R$^5$ and R$^6$ independently are selected from H, lower alkyl, aralkyl, acyl or sulfonyl.

2. A terpene derivative according to the formula

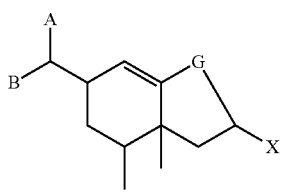

wherein G is

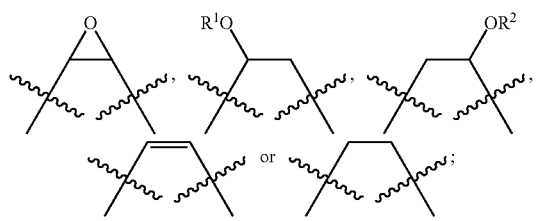

X is

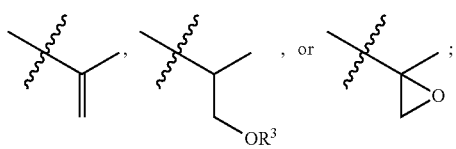

$R^1$, $R^2$ and $R^3$ independently are selected from H, acyl, lower alkyl or aralkyl; and
A and B independently are selected from an ester, an aromatic sulfonyl, a nitro or hydrogen.

3. A terpene derivative according to the formula

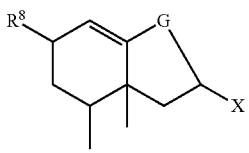

wherein G is

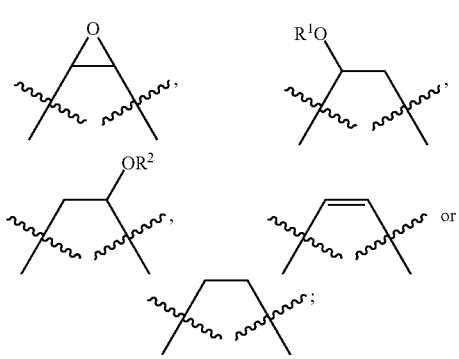

X is

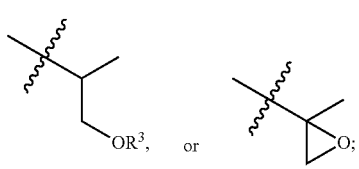

and
$R^1$, $R^2$ and $R^3$ independently are selected from H, acyl, lower alkyl or aralkyl;
$R^8$ is selected from

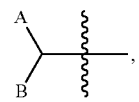

—$NR^5R^6$, $OR^4$ or —$N_3$, wherein A and B independently are selected from an ester, an aromatic sulfonyl, a nitro or hydrogen;
$R^4$ is independently selected from H, lower alkyl, aralkyl or acyl; and
$R^5$ and $R^6$ independently are selected from H, lower alkyl, aralkyl, acyl or sulfonyl.

4. The terpene derivative of claim 3, having the formula

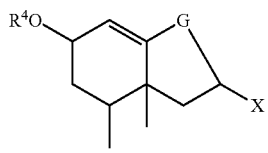

wherein $R^4$ represents an acyl group.

5. A terpene derivative having a formula

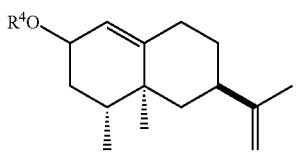

wherein $R^4$ is selected from lower alkyl or aralkyl.

6. The terpene derivative of claim 2 having the formula

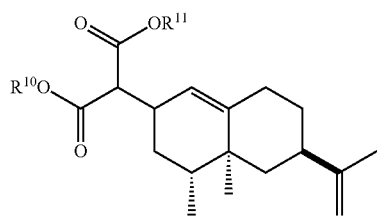

wherein $R^{10}$ and $R^{11}$ independently are selected from lower alkyl groups.

7. The terpene derivative of claim 1, having the formula

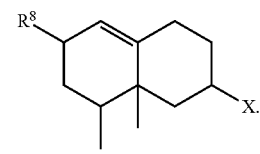

8. The terpene derivative of claim 1, having the formula

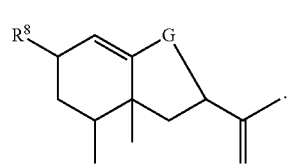

9. The terpene derivative of claim 7, wherein X is

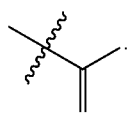

10. The terpene derivative of claim 2, having the formula

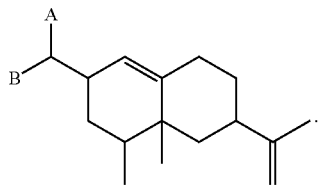

11. The terpene derivative of claim 10, having the formula

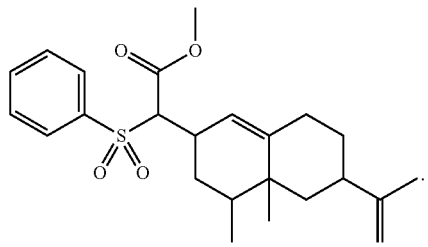 [SMILES: C=C(C)C1CCC2=CC(C(C(=O)OC)S(=O)(=O)c3ccccc3)CC(C)C2(C)C1]

12. The terpene derivative of claim 2, wherein G is

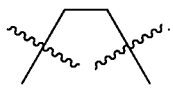

13. The terpene derivative of claim 2, wherein X is

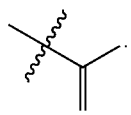

14. The terpene derivative of claim 2, wherein the terpene derivative is selected from

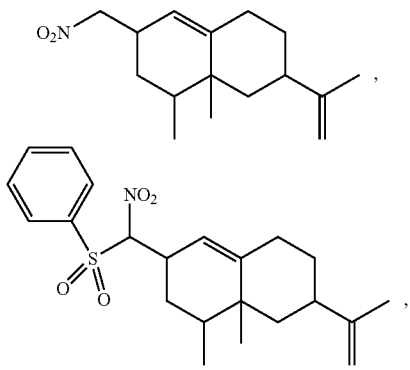

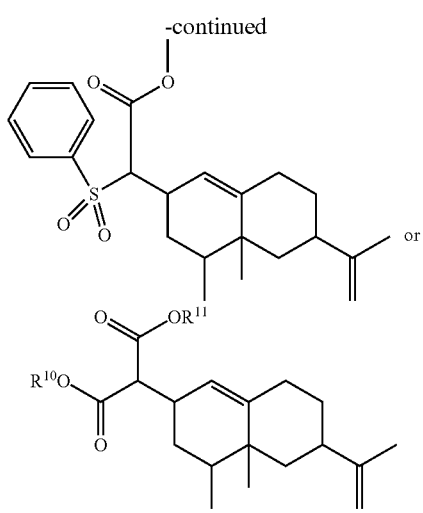

wherein $R^{10}$ and $R^{11}$ independently are selected from hydrogen or lower alkyl.

15. A terpene derivative according to the formula

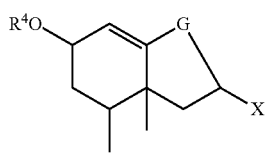

wherein G is

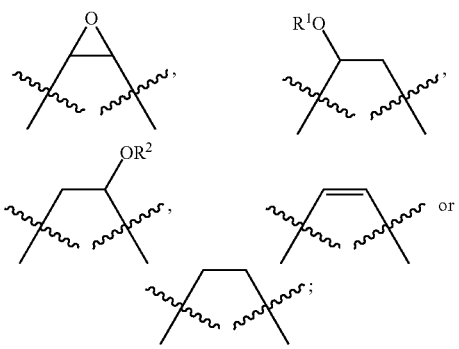

X is

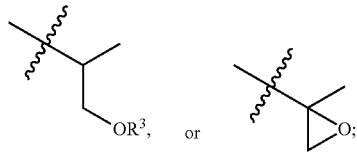

and $R^4$ is selected from lower alkyl or aralkyl.

* * * * *